(12) United States Patent
Kolb et al.

(10) Patent No.: US 6,960,216 B2
(45) Date of Patent: Nov. 1, 2005

(54) MODULAR DRILL GUIDE

(75) Inventors: Eric Kolb, Quincy, MA (US); Phil Tremblay, Taunton, MA (US); Jonathan Haylock, Orangevale, CA (US)

(73) Assignee: DePuy Acromed, Inc., Raynham, MA (US)

( * ) Notice: Subject to any disclaimer, the term of this patent is extended or adjusted under 35 U.S.C. 154(b) by 208 days.

(21) Appl. No.: 10/394,879

(22) Filed: Mar. 21, 2003

(65) Prior Publication Data

US 2004/0186482 A1 Sep. 23, 2004

(51) Int. Cl.⁷ .......................... A61B 17/58; A61F 2/00
(52) U.S. Cl. ........................................................ 606/96
(58) Field of Search ............................... 606/53, 86, 96, 606/97, 98, 87–89

(56) References Cited

U.S. PATENT DOCUMENTS

| | | | |
|---|---|---|---|
| 2,466,023 A | | 4/1949 | Griffin |
| 4,502,475 A | | 3/1985 | Weigle et al. |
| 4,686,972 A | | 8/1987 | Kurland |
| 5,049,150 A | * | 9/1991 | Cozad .................. 606/80 |
| 5,180,381 A | | 1/1993 | Aust |
| 5,303,694 A | | 4/1994 | Mikhail |
| 5,423,826 A | | 6/1995 | Coates et al. |
| 5,507,801 A | * | 4/1996 | Gisin et al. .................. 606/86 |
| 5,558,622 A | | 9/1996 | Greenberg |
| 5,603,713 A | | 2/1997 | Aust |
| 5,676,666 A | | 10/1997 | Oxland |
| 5,755,721 A | | 5/1998 | Hearn |
| 5,851,207 A | | 12/1998 | Cesarone |
| 6,235,034 B1 | | 5/2001 | Bray |
| 6,332,887 B1 | | 12/2001 | Knox |
| 6,342,056 B1 | | 1/2002 | Mac-Thiong et al. |
| 6,342,057 B1 | | 1/2002 | Brace et al. |
| 6,379,364 B1 | | 4/2002 | Brace et al. |
| 6,416,518 B1 | | 7/2002 | DeMayo |
| 6,419,678 B1 | | 7/2002 | Asfora |
| 6,565,571 B1 | | 5/2003 | Jackowski |
| 6,592,586 B1 | * | 7/2003 | Michelson .................. 606/71 |
| 6,712,818 B1 | | 3/2004 | Michelson |
| 2001/0047172 A1 | | 11/2001 | Foley |
| 2002/0049444 A1 | | 4/2002 | Knox |
| 2002/0082606 A1 | | 6/2002 | Suddaby |
| 2003/0233098 A1 | | 12/2003 | Markworth |
| 2004/0015174 A1 | | 1/2004 | Null |
| 2004/0092947 A1 | | 5/2004 | Foley |

FOREIGN PATENT DOCUMENTS

| | | |
|---|---|---|
| WO | WO 03/007826 | 1/2003 |
| WO | WO-03/024344 | 3/2003 |

* cited by examiner

Primary Examiner—Eduardo C. Robert
Assistant Examiner—Anu Ramana
(74) Attorney, Agent, or Firm—Nutter McClennen & Fish LLP

(57) ABSTRACT

A modular drill guide for use in securing a spinal fixation plate to a spine is provided. The drill guide generally includes a shaft having a proximal end and a distal end adapted to engage a spinal fixation plate, and at least one guide member removably and replaceably matable to the shaft. The guide member can have a connector member with at least one bore extending therethrough for receiving at least a portion of the shaft, and at least one barrel formed thereon and defining a lumen for receiving a tool, such as an awl, a drill bit, a fastener, or a driver device. The shaft can optionally be coupled to an elongate member having a proximal end and a distal end. The barrel(s) include a bore formed therethrough for receiving a tool.

28 Claims, 10 Drawing Sheets

MODULAR DRILL GUIDE

FIELD OF THE INVENTION

The present invention relates to devices for assisting in spinal surgery, and more particularly to a modular drill guide for introducing spinal tools and devices.

BACKGROUND OF THE INVENTION

Advancing age, as well as injury, can lead to changes in the bones, discs, joints, and ligaments of the spine, producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots to allow for freedom of screw movement. The bone plate is placed against the damaged vertebral bodies and bone screws are used to secure the bone plate to the spine and optionally to a prosthetic implant or bone graft positioned between the adjacent vertebrae. Implantation of the plate, however, can be difficult. Each plate must be properly aligned with the vertebral bodies, and holes for receiving the bone screws must be drilled into the vertebrae at precise angles. It is often necessary to use the bone plate as a drill guide for drilling and tapping the bone in preparation for receiving the bone screws. Such a procedure can be difficult, however, as the surgeon is required to securely and rigidly hold the bone plate against the vertebrae, obtain proper alignment, drill, tap, and finally set the bone screws.

Accordingly, there remains a need for a drill guide instrument which can be used to assist in fastening a plate to a patient's spine.

SUMMARY OF THE INVENTION

The present invention generally provides a modular drill guide having an elongate member, a shaft coupled to the elongate member and having a distal mating end adapted to mate to a spinal fixation plate, and at least one guide member removably mated to the elongate member. The guide member includes at least one barrel formed therein and defining a bore for receiving a tool. The guide member is preferably slidably matable onto the elongate member in a proximal-to-distal direction. A stop member can be formed on at least one of the guide member and the elongate member to prevent distal movement of the guide member, with respect to the elongate member, beyond a particular position.

The elongate member can have a variety of configurations, but it preferably has an inner lumen extending therethrough between proximal and distal ends, and the shaft is preferably rotatably disposed within the inner lumen of the elongate member. The elongate member can optionally include a locking element effective to prevent rotation of the shaft with respect to the elongate member. The modular drill guide can also include a mating element disposed between the elongate member and the guide member for removably mating the guide member to the elongate member. The mating element can have a variety of configurations and can have, for example, an interference fit, a dovetail connection, a snap-fit connection, and a tongue-and-groove connection. In an exemplary embodiment, the mating element comprises one of a female and a male dovetail element formed on the guide member, and the other one of a male and a female dovetail element formed on the elongate member.

In another embodiment, the distal mating end of the shaft includes an engagement mechanism formed thereon for mating with a spinal fixation plate. The engagement mechanism can comprise threads, a hook member, a twist-lock member, or a snap-fit member. In yet another embodiment, the distal end of at least one of the elongate member and the guide member includes an alignment mechanism adapted to align the modular drill guide with a spinal fixation plate engaged by the distal mating end of the shaft. The alignment mechanism can be at least one protrusion adapted to fit within a corresponding detent formed on a spinal fixation plate, and at least one flange adapted to be positioned adjacent an edge of a spinal fixation plate.

In other aspects, the guide member includes first and second barrels, and a connector having a mating element formed thereon for mating the guide member to the elongate member. The mating element is preferably formed on a proximal end of the connector. The mating element can have a snap-fit connection, or it can comprise a T-slot formed in the connector and effective to mate to a corresponding T-shaped element disposed on the elongate member. The T-slot preferably extends between proximal and distal ends of the connector such that the connector mates to the elongate member in a proximal-distal direction. A stop member can optionally be formed in at least one of the T-slot and the T-shaped element to prevent distal movement of the connector with respect to the elongate member beyond a particular position. The T-slot can also include a retaining element disposed therein for temporarily securing the guide member to the elongate member. The retaining element preferably comprises a ball plunger adapted to sit in a corresponding detent formed on the elongate member.

In yet another embodiment, a modular drill guide is provided having a shaft with a proximal end and a distal end adapted to engage a spinal fixation plate. At least one guide member is removably and replaceably matable to the shaft. The guide member has a connector member with at least one bore extending therethrough for receiving at least a portion of the shaft, and at least one barrel formed thereon and defining a lumen for receiving a tool. The modular drill guide can also include a mating body for removably and replaceably mating the guide member to the shaft. The mating body preferably includes a proximal end and a distal end, and an inner lumen formed therein for receiving at least a portion of the shaft. The connector member can have a generally elongate cylindrical shape with a distal end, and a proximal end adapted to removably mate to the distal end of the mating body. The shaft can optionally extend through the bore in the connector member and through the inner lumen in the mating body when the guide member is mated to the mating body.

In another embodiment, a modular drill guide kit is provided having an elongate member with a proximal, handle end and a distal mating end adapted to removably mate to a spinal fixation plate. A plurality of guide members are removably and replaceably matable to the elongate member. Each guide member has at least one barrel formed thereon and disposed at a predetermined angle with respect to a longitudinal axis of the elongate member. Each of the plurality of guide members further includes at least one barrel with a predetermined angle different from the predetermined angle of the at least one barrel formed on another one of the plurality of guide members.

BRIEF DESCRIPTION OF THE DRAWINGS

The invention will be more fully understood from the following detailed description taken in conjunction with the accompanying drawings, in which.

DETAILED DESCRIPTION OF THE INVENTION

In general, the present invention provides a modular drill guide for use in securing a spinal fixation plate to a spine. The drill guide generally includes a shaft having a proximal end and a distal end adapted to engage a spinal fixation plate, and at least one guide member removably and replaceably matable to the shaft. The guide member can have a connector member with at least one bore extending therethrough for receiving at least a portion of the shaft, and at least one barrel formed thereon and defining a lumen for receiving a tool, such as an awl, a drill bit, a fastener, or a driver device. The shaft can optionally be coupled to an elongate member having a proximal end and a distal end. The modular drill guide is particularly effective in that it facilitates the placement of a spinal fixation plate along a patient's spine without hindering the surgeon's visual access to the surgical site. The modular nature of the drill guide is also advantageous as it allows a surgeon to select from several drill guides having barrels with varying lengths to limit the depth of penetration, and/or drill guides having barrels oriented at varying angles to control the trajectory of the fastening element being implanted.

Figure 1:
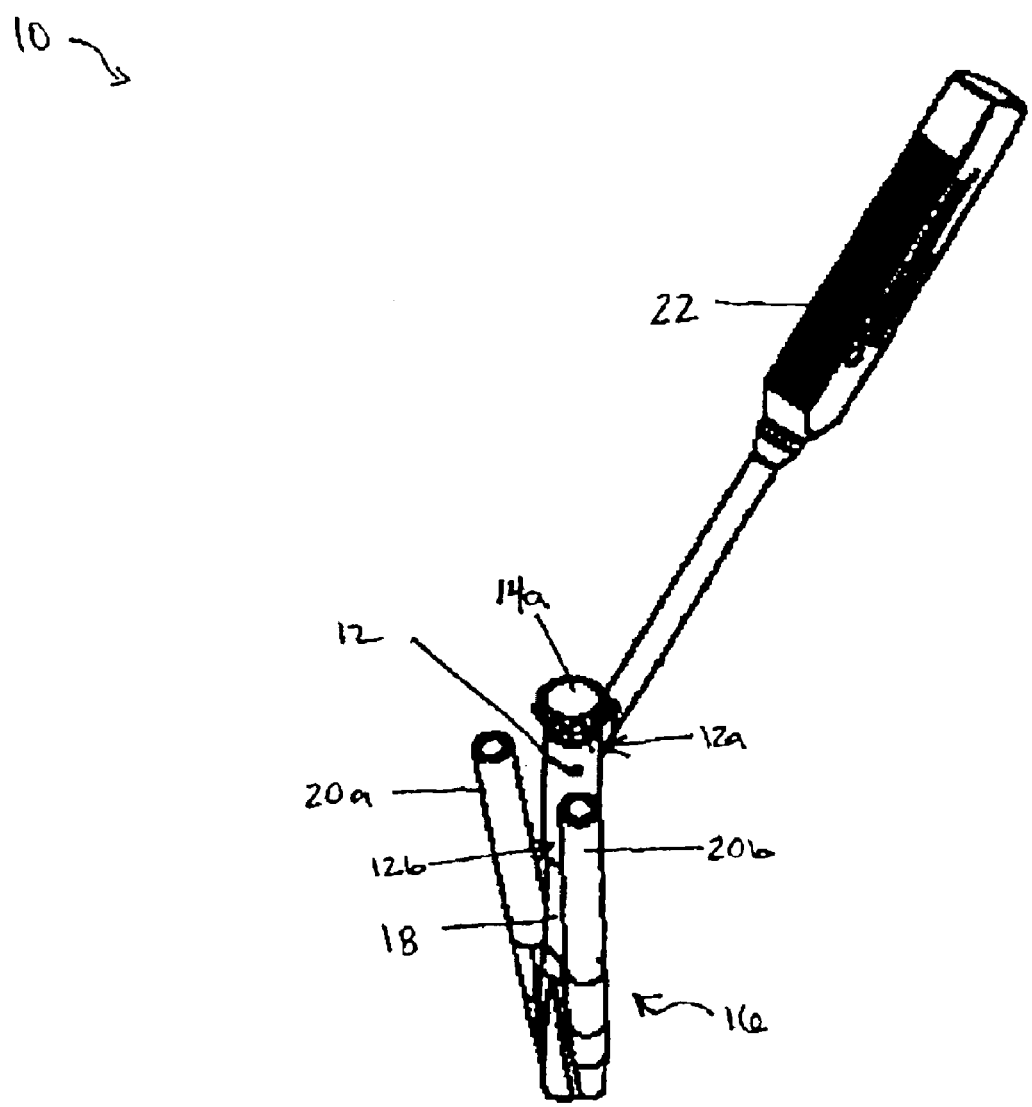
FIG. 1 is a perspective view of a modular drill guide according to one embodiment of the present invention.

FIG. 1 illustrates one embodiment of a modular drill guide 10 including an elongate member 12 having a proximal end 12a, a distal end 12b, and an inner lumen 12c (shown in FIG. 2) extending therethrough. A shaft 14 (shown in FIG. 3) is rotatably disposed within the inner lumen 12c of the elongate member 12 and includes a proximal end 14a, and a distal mating end 14b. The distal mating end 14b of the shaft 14 is adapted to mate to a spinal fixation plate. The modular drill guide 10 further includes a guide member 16 that is removably and replaceably mated to the elongate member 12 and having two barrels 20a, 20b formed thereon or mated thereto. The drill guide 10 can also include a handle 22 mated to the elongate member 12 for grasping and manipulating the device 10.

Figure 2:
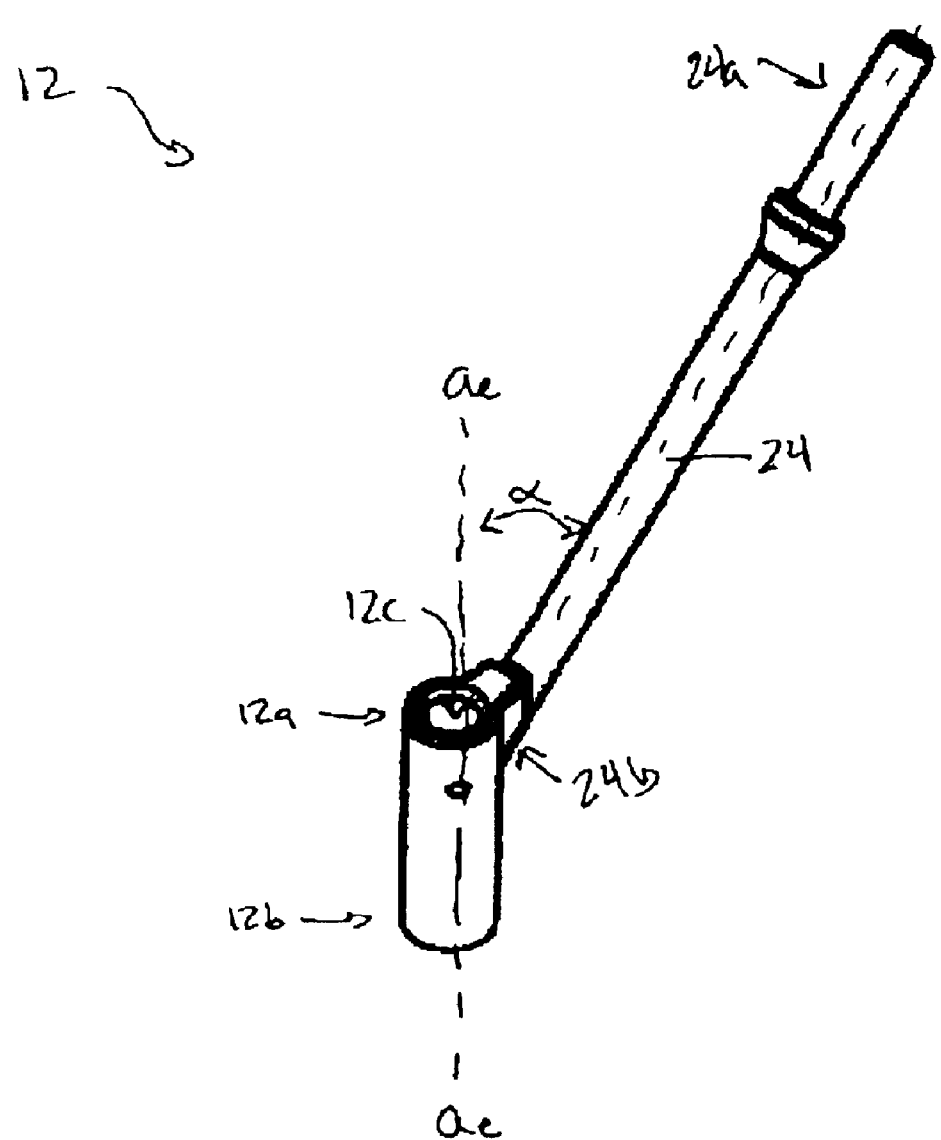
FIG. 2 is a perspective view of the elongate member portion of the modular drill guide shown in FIG. 1.

FIG. 2 illustrates the elongate member 10 in more detail. As shown, the elongate member 12 has a generally cylindrical shape and includes a proximal end 12a, a distal end 12b, and an inner lumen 12c extending therethrough and adapted to rotatably receive the shaft 14 of the modular drill guide 10. The distal end 12b of the elongate member 12 is adapted to mate to the guide member 16, and thus preferably includes a mating element formed within the distal portion 12b of the inner lumen 12c to mate to a corresponding mating element formed on the guide member 16, as will be discussed in more detail with respect to FIG. 4.

The elongate member 12 can also optionally include a sidearm 24 mated thereto for grasping and manipulating the device 10. The sidearm 24 includes a proximal end 24a and a distal end 24b, and preferably extends at an angle $\alpha$ in a proximal direction with respect to a central axis $a_e$ of the elongate member 12 to provide visual access to the surgical site. The angle $\alpha$ of the sidearm 24 can optionally be adjustable with respect to the longitudinal axis $a_e$ of the elongate member 12. The proximal end 24a of the sidearm 24 can include a handle member 22 (shown in FIG. 1) mated thereto to facilitate grasping of the sidearm 24, and the distal end 24b of the sidearm 24 can be fixedly or rotatably mated to the elongate member 12. Preferably, the sidearm 24 rotates around the central axis $a_e$ of the elongate member 12 to allow the surgeon to more easily manipulate the device 10. A locking mechanism can be provided for preventing rotation of the sidearm 24 with respect to the elongate member 12 if desired. Alternatively, the sidearm 24 can be configured such that connection of the shaft 14 to a spinal fixation plate is effective to prevent rotation of the sidearm 24 with respect to the elongate member 12. By way of non-limiting example, the distal end 24b of the sidearm 24 can include a ring-shaped member (not shown) adapted to fit around an annular groove (not shown) formed in the proximal end 12a of the elongate member 12 to allow rotation of the sidearm 24 with respect to the elongate member 12. The shaft 14 can optionally includes a proximal knob (shown in FIG. 3) that, upon connection of the shaft 14 to a spinal fixation plate, applies a force to the ring-shaped member of the sidearm 24 to prevent rotation of the sidearm 24.

A person having ordinary skill in the art will appreciate that while a substantially cylindrical elongate member 12 is shown, the elongate member 12 can have virtually any shape and size, and it does not need to include an inner lumen for receiving the shaft 14. The shaft 14 can be mated to any portion of the elongate member 12, and a variety of mechanisms can be provided for allowing rotation of the shaft 14 with respect to the elongate member 12. Moreover, the elongate member 12 can include a variety of features to facilitate grasping thereof, and it need not include a sidearm 24 and/or a handle member 22.

Figure 3:
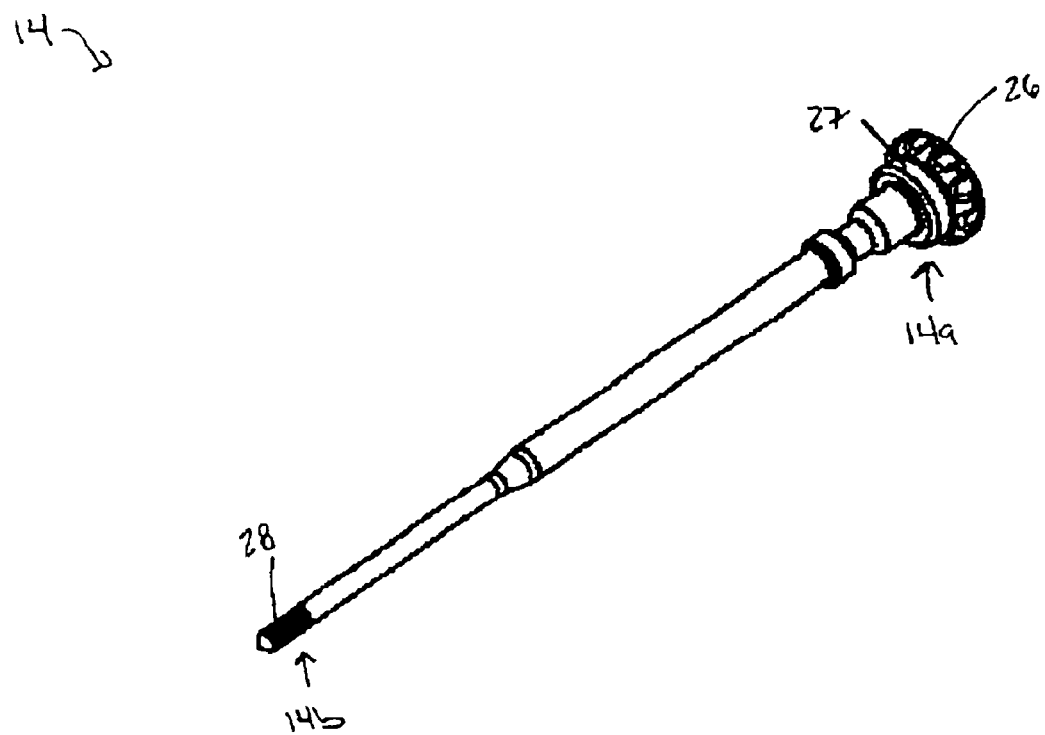
FIG. 3 is a perspective view of the shaft portion of the modular drill guide shown in FIG. 1.

The shaft 14 is shown in more detail in FIG. 3 and includes a proximal end 14a and a distal end 14b. The proximal end 14a can have a knob 26 or other member formed thereon to allow the shaft 14 to be grasped and rotated within the inner lumen 12c of the elongate member 12. The knob 26 can also be effective to bear down on the elongate member 12 to prevent further rotation or other movement of the elongate member 12 with respect to the shaft 14. As shown in FIG. 3, the knob 26 includes an annular ring 27 that is adapted to abut the proximal end 12a of the elongate member 12, as shown in FIG. 1. A person having ordinary skill in the art will appreciate that a variety of techniques can be used to prevent movement of the elongate member 12 with respect to the shaft 14.

The distal end 14b of the shaft 14 includes an engagement mechanism 28 formed thereon and effective to grasp a spinal fixation plate. The engagement mechanism 28 can have a variety of configurations and can be, for example, threads adapted to mate with corresponding threads formed in a bore in a fixation plate, a hook member adapted to grasp a portion of a fixation plate, a twist-lock member adapted to lock onto a corresponding twist-lock member formed in a fixation plate, and a snap-fit member adapted to snap onto a fixation plate. A person having ordinary skill in the art will appreciate that virtually any type of engagement mechanism can be used to at least temporarily secure the shaft 14 to a spinal fixation plate. Moreover, engagement of the shaft 14 to a spinal fixation plate can be accomplished using techniques other than rotation of the shaft. The shaft 14 can, for example, include a lever effective to apply a cam action against the elongate member.

Figure 4:
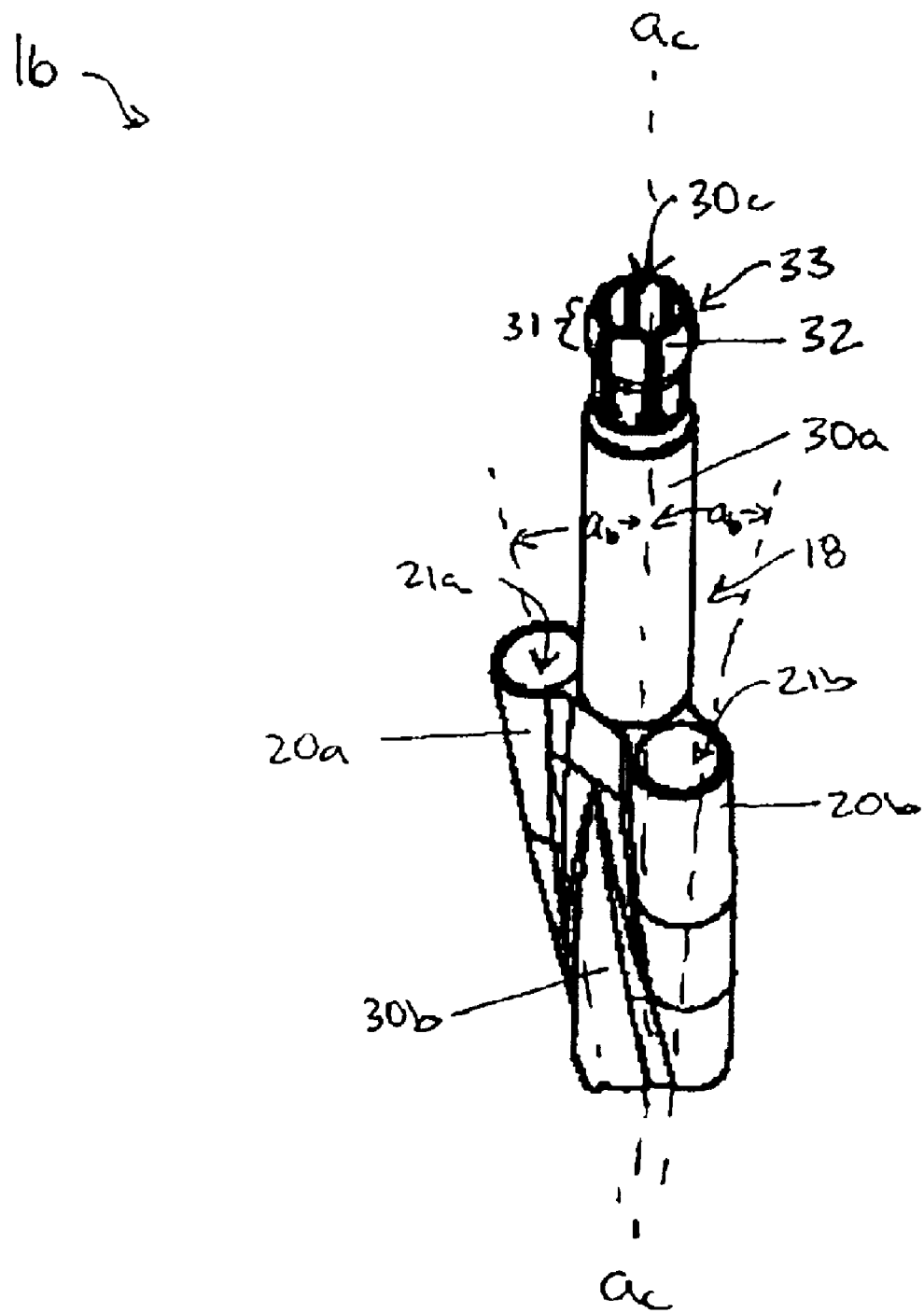
FIG. 4 is a perspective view of the guide member portion of the modular drill guide shown in FIG. 1.
Figure 5:
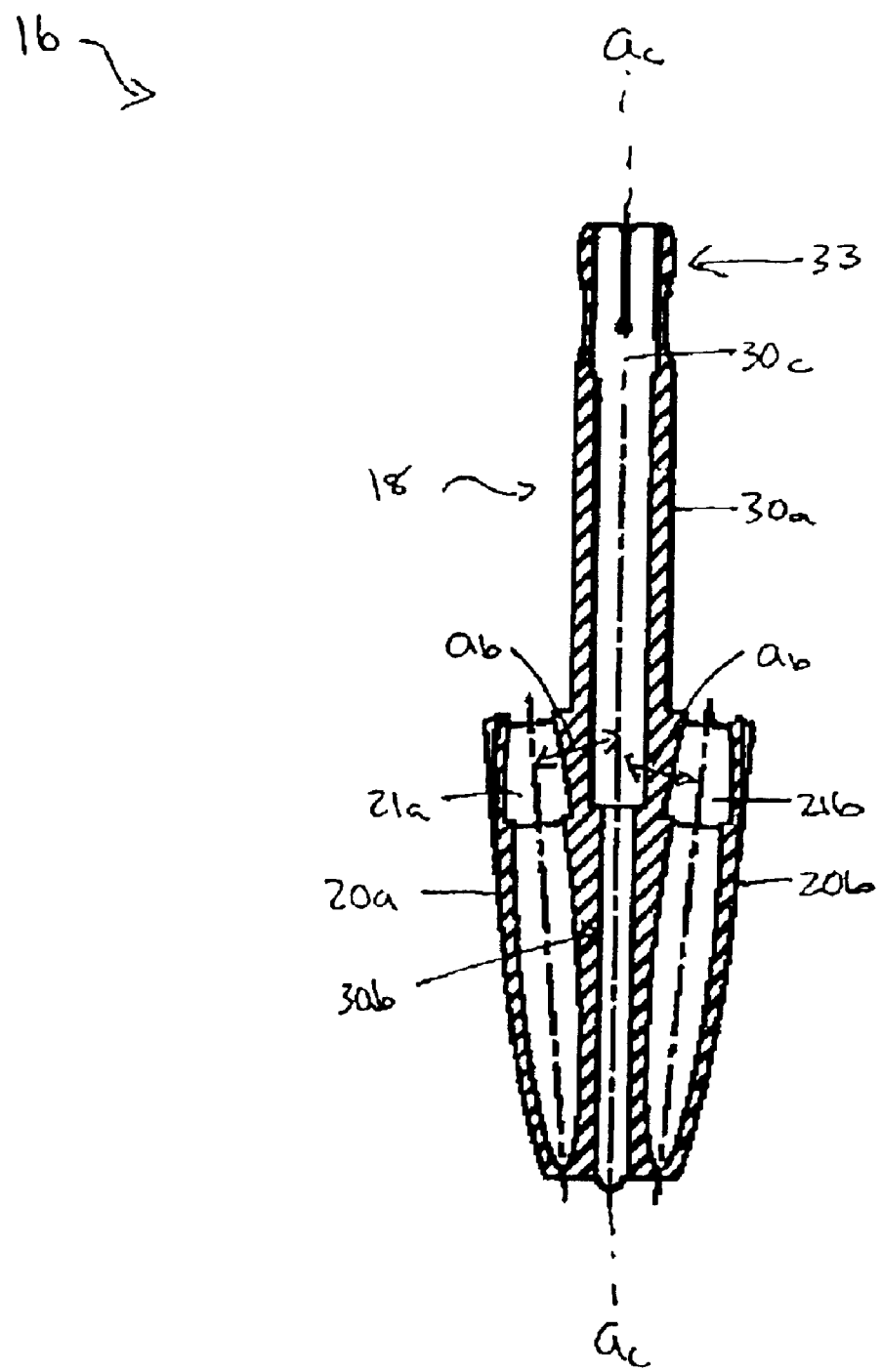
FIG. 5 is a cross-sectional view of the guide member shown in FIG. 4.

Referring now to FIGS. 4 and 5, the guide member 16 is shown in more detail and includes a connector 18 having two barrels 20a, 20b formed thereon. The connector 18 includes a proximal portion 30a, a distal portion 30b, and an inner lumen 30c extending therethrough and effective to receive a portion of the shaft 14. The proximal portion 30a of the connector 18 includes a mating element 33 formed on the proximal-most end thereof for mating to a corresponding mating element formed on the distal end 12b of the elongate member 12. The mating element can utilize a variety of connections to mate the guide member 16 to the elongate member 12 including, for example, an interference fit, a dovetail connection, a snap-fit connection, and a tongue-and-groove connection. Moreover, the mating element can be formed at any location on the guide member 16, and it is not limited to being formed on the proximal end 30c of the connector 18. As shown in FIG. 4, the mating element 33 on the proximal end 30a of the guide member 16 is in the form of a snap-fit connection having several flexible arms 32 which deform upon insertion of the mating element 33 into the inner lumen 12c of the elongate member 12, and once fully inserted, expand to engage the elongate member 12.

The inner lumen 12c of the elongate member 12 can include an annular groove (not shown) formed therein for receiving an annular ridge 31 formed on the mating element 33 of the guide member 16.

The distal portion 30b of the connector 18 is preferably positioned between the two barrels 20a, 20b. The barrels 20a, 20b can be attached to the connector 18 at any location, and can be either integrally formed with the connector, mated thereto, or removably attached thereto. Each barrel 20a, 20b includes an inner lumen 21a, 21b extending therethrough for receiving a tool. Each inner lumen 21a, 21b defines a predetermined angle $a_b$ with respect to the longitudinal axis $a_c$, $a_e$, of the connector 18 and the elongate member 12. The angle $a_b$ defines the entry angle for a tool being inserted through the barrel 20a, 20b. While the angle $a_b$ can vary, the angle $a_b$ of each barrel 20a, 20b is preferably in the range of about 0° to 15°.

A person having ordinary skill in the art will appreciate that while two barrels 20a, 20b are illustrated, the guide member 16 can include any number of barrels. Moreover, the barrels can also have a variety of configurations, shapes, and sizes. By way of non-limiting example, the barrels 20a, 20b can include a removable proximal portion and a distal portion fixedly attached to the connector. The proximal portion can merely slide onto and off of the distal portion to allow barrels having different lengths to be attached to the device. Virtually any connection technique can be used to connect the proximal and distal barrel portions.

Figure 6:
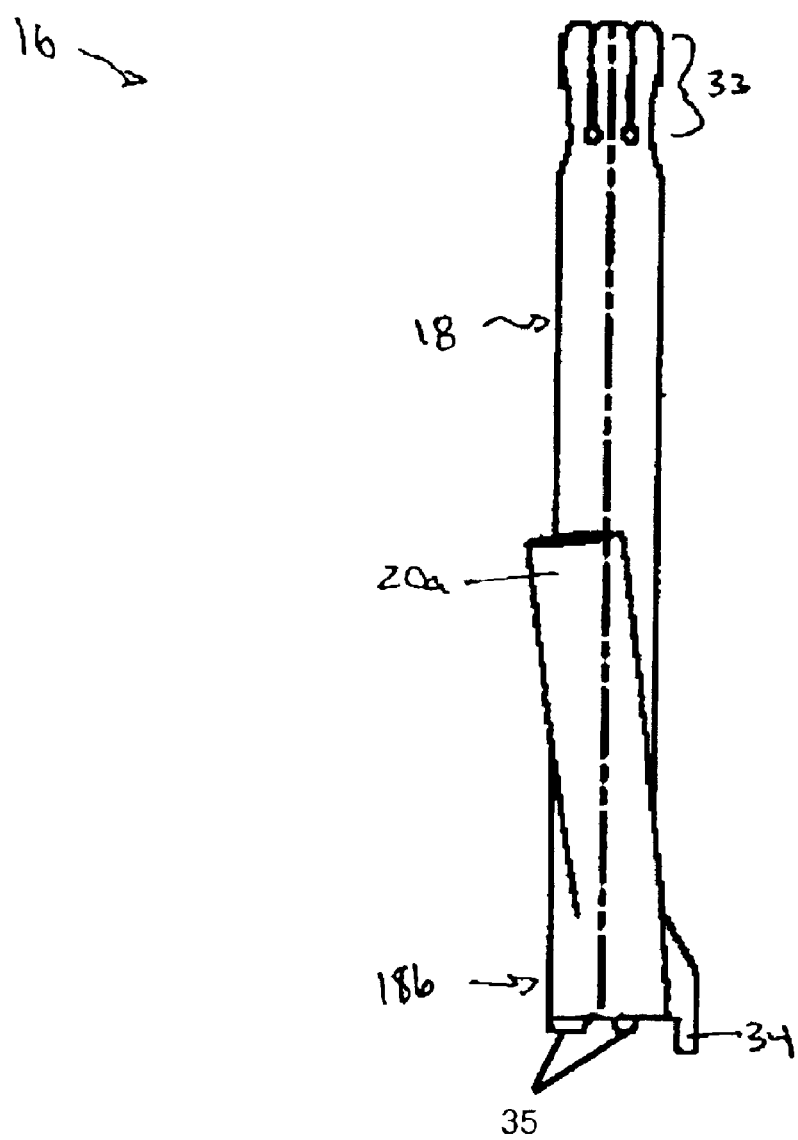
FIG. 6 is a side view of the guide member shown in FIG. 4.

Referring now to FIG. 6, the guide member 16 can also optionally include an alignment mechanism formed on a distal end thereof for aligning the modular drill guide 10 with respect to a spinal fixation plate being engaged by the shaft 14. The alignment mechanism can have a variety of configurations, but should be adapted to align the modular drill guide 10 so that the angle $a_b$ of each barrel 20a, 20b is properly aligned with respect to the planar surface of the fixation plate. FIG. 6 illustrates one embodiment of an alignment mechanism in the form of a flange 34 adapted to be positioned adjacent an edge of a spinal fixation plate. The flange 34 is preferably a flattened extension formed on the distal end of the connector 18. In another embodiment, the alignment mechanism can be one or more protrusions 35 adapted to fit within a corresponding detent (not shown) formed on a spinal fixation plate. Alternatively, the alignment mechanism can be formed from one or more raised features formed on the distal-most end 18b of the connector 18 and effective to extend into and engage a longitudinally running groove extending along a midline of a fixation plate. A person having ordinary skill in the art will appreciate that a variety of techniques can be used to align the modular drill guide 10 with respect to a fixation plate.

Figure 7:
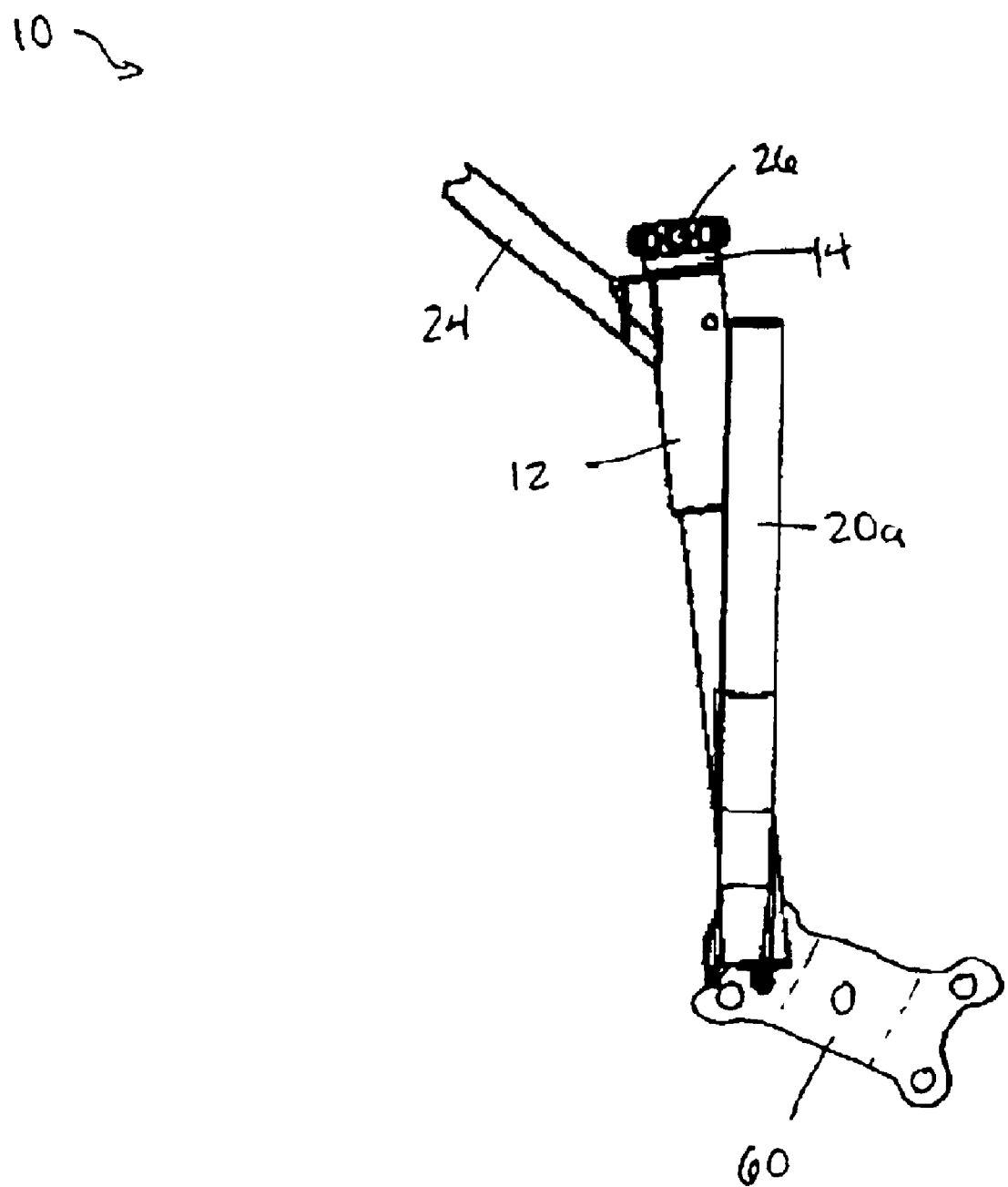
FIG. 7 is a side view of a portion of the modular drill guide shown in FIG. 1 and a spinal fixation plate.

Referring now to FIG. 7, in use, the modular drill guide 10 can be provided with a variety of guide members, each having barrels 20a, 20b positioned at varying angles and having varying lengths to limit the depth of penetration of a tool being inserted therethrough. Preferably, several guide members adapted to position one or more barrels at various angles in the range of about 0° to 15° are provided, and a separate set of barrels having varying lengths are provided. The surgeon can thus select the guide member with the appropriate angle, and then attach barrels having the appropriate length to the guide member. The surgeon then attaches a spinal fixation plate 60 to the distal end of the shaft 14 by rotating or otherwise moving the shaft 14 to engage the plate 60. The alignment mechanism can be used to ensure proper alignment of the drill guide with respect to the plate. The barrels should be aligned with the apertures formed in the plate that are adapted to receive the fastening element for fixing the plate to a patient's spine. Preferably, the barrels are adapted to be positioned adjacent two apertures formed on either the superior side of the plate or the inferior side of the plate. The barrels can come into contact with the plate, or they can be positioned at some location proximal to the plate. Once the drill guide is attached and properly aligned with a fixation plate, the plate can then be positioned with respect to a patient's spine and one or more tools can be inserted through the barrel to attach the plate to the spine. Preferably, a drill is then inserted through each barrel to create a bore or pilot hole in the vertebrae. A fastening element, such as a spinal screw, can then be inserted through each barrel followed by a driver tool effective to drive the screw into the drilled bore. A person having ordinary skill in the art will appreciate that, while a modular drill guide is described, a single drill guide having barrels fixed thereto can be provided. In such an embodiment, the drill guide is preferably used with several drills, each having drill bits with varying lengths.

Figure 8:
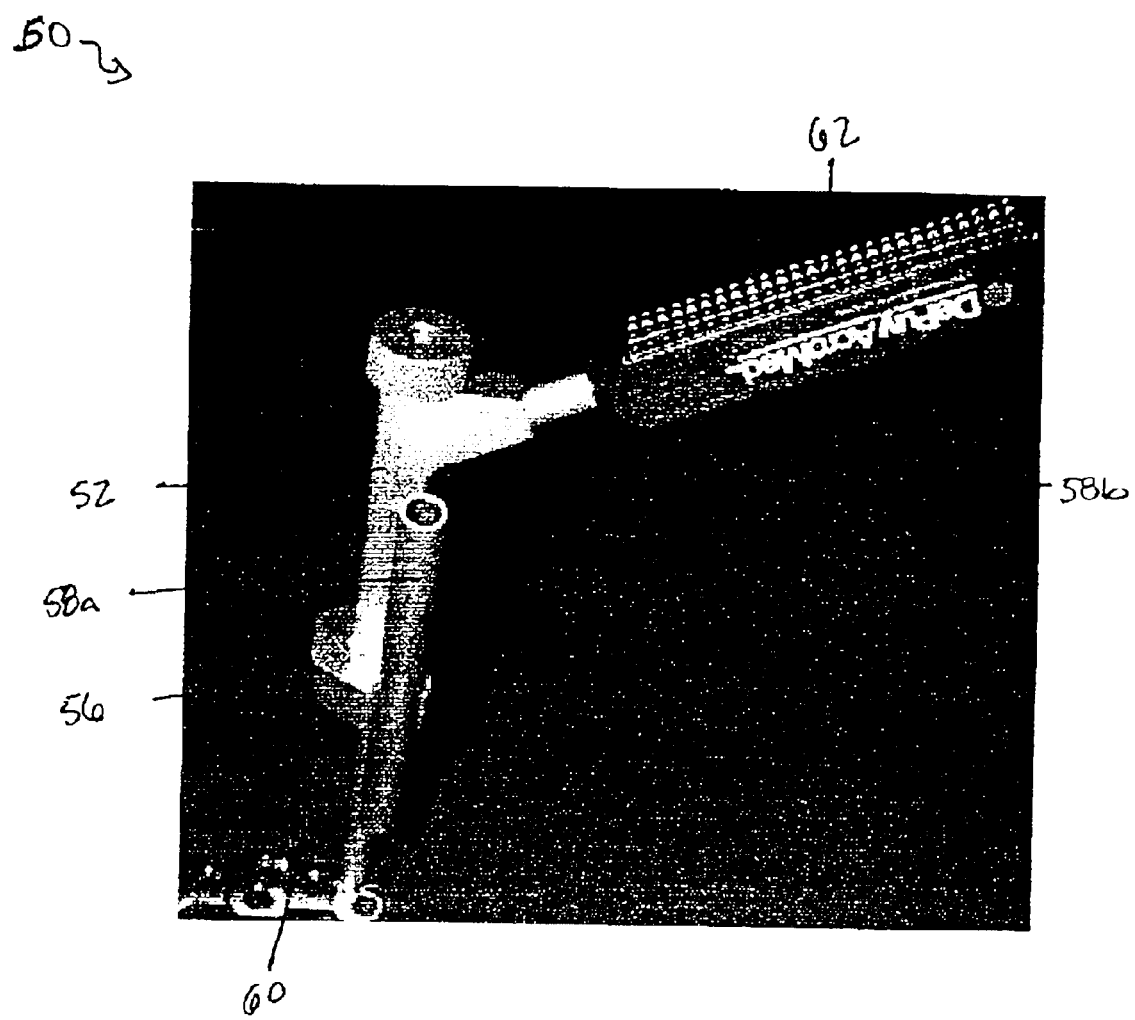
FIG. 8 is a perspective view of another embodiment of a modular drill guide and a spinal fixation plate according to the present invention.

FIG. 8 illustrates another embodiment of a modular drill guide 50. As shown, the drill guide 50 includes an elongate member 52 having a handle 62 mated thereto, a guide member 56 removably mated to the elongate member 52, and a shaft 54 (shown in FIG. 10) extending through the elongate member 52 and having a distal end adapted to mate to a spinal fixation plate 60. The guide member 56 is slidably matable to the elongate member 52, preferably in a proximal-to-distal direction, and includes first and second barrels 58a, 58b formed thereon and adapted to receive a tool. In an exemplary embodiment, the device 50 is provided as a kit containing several guide members 56 having barrels 58a, 58b positioned at varying angles and/or having varying lengths, as will be described in more detail with respect to FIG. 12.

Figure 9A:
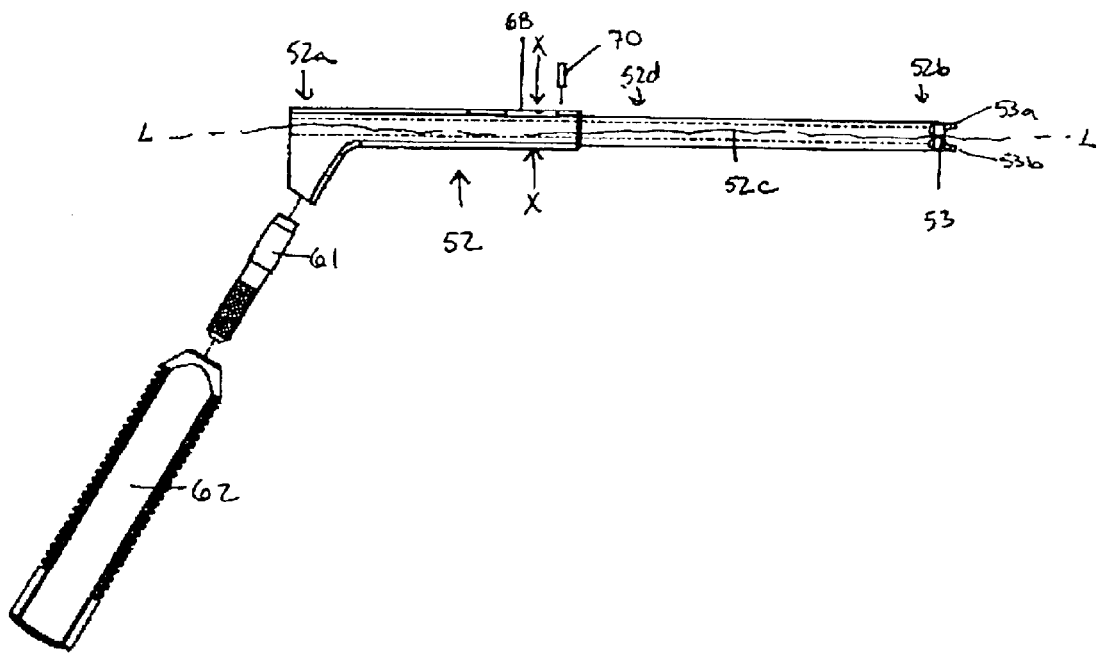
FIG. 9A is a perspective view of the elongate member, handle, and shaft of the modular drill guide shown in FIG. 8.

The elongate member 52 is shown in more detail in FIG. 9A, and includes a proximal end 52a, a distal end 52b, and an inner lumen 52c extending therebetween and adapted to receive at least a portion of the shaft 54. The proximal end 52a of the elongate member 52 can include a sidearm 61 and handle member 62, similar to sidearm 24 and handle member 22 previously described with respect to FIGS. 1 and 2, mated thereto, and the distal end of the elongate member 52 can include an alignment mechanism 53 formed thereon. The alignment mechanism 53 can be similar to alignment mechanism 34 described above with respect to FIG. 6, and is effective to align the device 50 with respect to a plate 60 being engaged by the shaft 54. As shown in FIG. 9A, the alignment mechanism 53 includes opposed protrusions or arms 53a, 53b that fit within corresponding detents formed in the fixation plate 60. A person having ordinary skill in the art will appreciate that virtually any mechanism can be used to align the device 50 with respect to a fixation plate. Moreover, the alignment mechanism can be formed on any portion of the device, and is not limited to being formed on a distal end of the elongate member 52 or the guide member 56.

Figure 9B:
FIG. 9B is a cross-sectional view of the elongate member taken across line X—X shown in FIG. 9A.
Figure 9B:
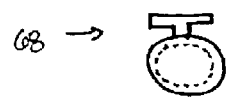

The elongate member 52 further includes a mating element 68 formed thereon for receiving the guide member 56. The mating element 68 can have a variety of configurations, but is preferably in the form of a dovetail connection that allows the guide member 56 to slide onto the elongate member 52 in a proximal-to-distal direction. In an exemplary embodiment, shown in FIG. 9B, the mating element is a T-shaped member 68 formed on a mid-portion 52d of the elongate member 52. The T-shaped member 68 is effective to slide into a corresponding T-shaped slot formed in the guide member 56, as will be described with respect to FIG. 11. A person having ordinary skill in the art will appreciate that while FIG. 9B illustrates a substantially cylindrical elongate member 52, the elongate member 52 can have any cross-sectional shape, such as square, rectangular, etc.

The elongate member 52 further preferably includes a stop member effective to prevent distal movement of the guide member 56 beyond a particular position. As shown in FIG. 9A, the stop member is a pin 70 positioned at a distal-most end of the mating element 68. The pin 70 is preferably positioned to prevent the barrels 58a, 58b from moving distally past the distal end 52b of the elongate member 52. The pin 70 can, however, be adapted to allow the barrels 58a, 58b to contact a fixation plate mated to the shaft 56.

Figure 10:
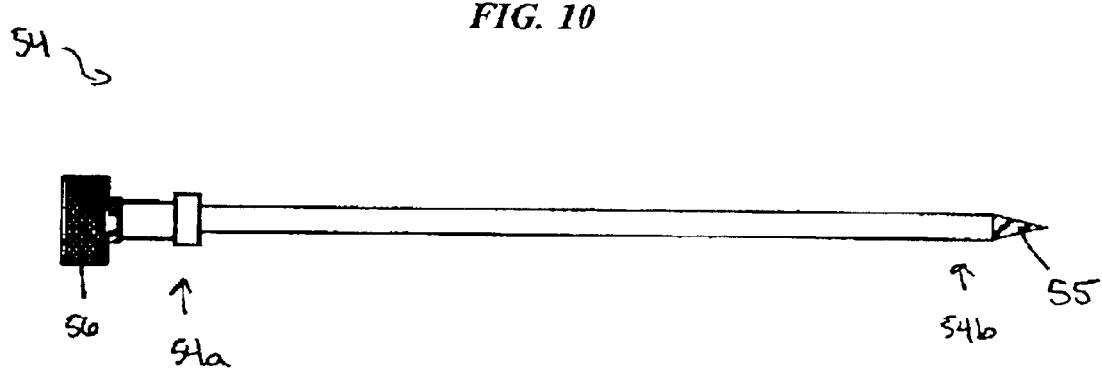
FIG. 10 is a side view of the shaft portion of the modular drill guide shown in FIG. 8.

The shaft 54, shown in more detail in FIG. 10, includes a proximal end 54a and a distal end 54b. The shaft 54 is adapted to be rotatably disposed through the lumen 52c formed in the elongate member 52, and thus it can include a knob 56 or other type of grasping mechanism effective to allow the shaft 54 to be grasped and rotated with respect to the elongate member 52. Preferably, the shaft 54 is fixedly connected to, yet rotatably disposed within, the elongate member 52 to prevent removal of the shaft 54 from the elongate member 52. The distal end 54b of the shaft 54 is adapted to mate to a fixation plate, such as plate 60 shown in FIG. 8, and thus it can include an engagement mechanism formed thereon. As shown in FIG. 10, the engagement mechanism 55 may take the form of threads adapted to mate with corresponding threads formed in a bore in a fixation plate. A person having ordinary skill in the art will appreciate that a variety of engagement mechanisms can be used, and that the engagement mechanism is not limited to being formed on the distal end 54b of the shaft 54.

While FIG. 10 illustrates the knob 56 mated to the shaft 54, the knob 56 can optionally be rotatably mated to the proximal end 52a of the elongate member 52 shown in FIG. 9A. In this embodiment, the knob 56 is adapted to mate to the proximal end 54a of the shaft 54, and thus the knob 56 and the shaft 54 can includes threads formed thereon. The device can be assembled by inserting the shaft 54 into the distal end 52b of the elongate member 52, and rotating the knob 56 to engage the shaft 54 and thereby retain the shaft 54 within the elongate member 52.

Figure 11:
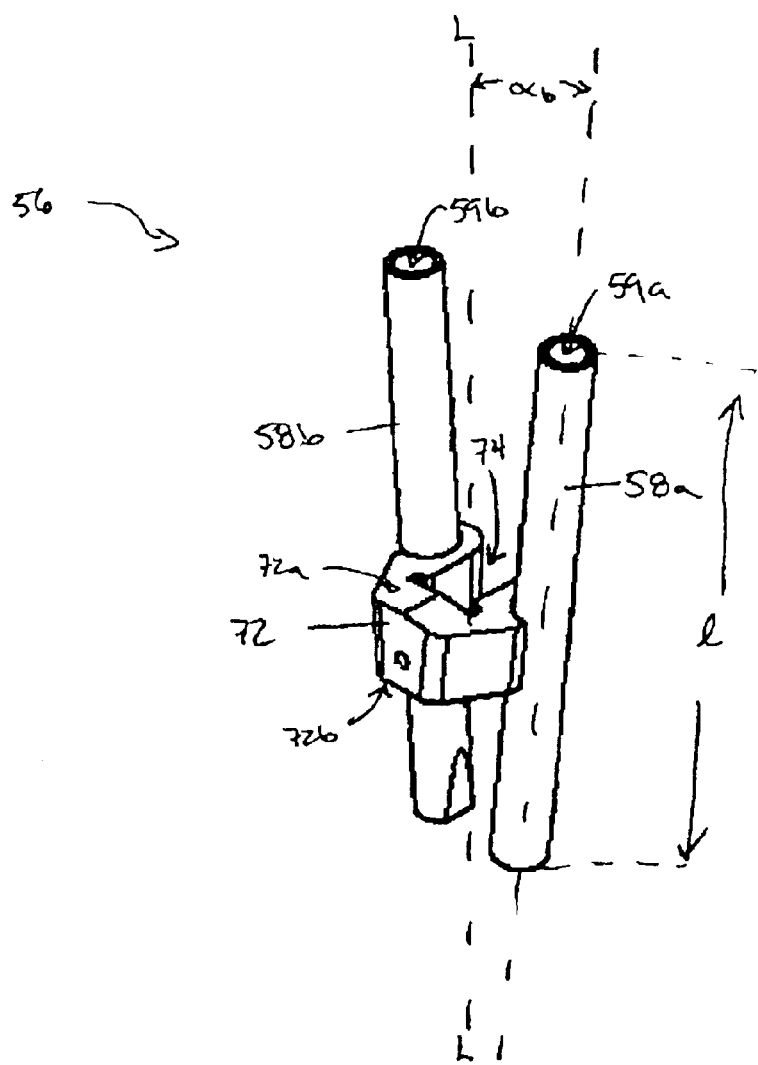
FIG. 11 is a perspective view of the guide member component of the modular drill guide shown in FIG. 8.

FIG. 11 illustrates the guide member 56 in more detail. As shown, the guide member 56 includes a connector 72 and first and second barrels 58a, 58b mated to the connector 72. While 15 two barrels 58a, 58b are shown, the guide member 56 can include one or more than two barrels. The barrels 58a, 58b can be fixedly or removably mated to the connector 72, and each barrel 68a, 68b includes a lumen 59a, 59bextending therethrough for receiving a tool. The barrels 68a, 68b are similar to barrels 20a, 20b described above with respect to FIGS. 4 and 5, and thus can extend at a predetermined angle $\alpha_b$ with respect to a longitudinal axis L (shown in FIG. 9A) of the device 50. Preferably, the device 50 is provided as a kit having several connectors 72 which are adapted to retain barrels 58a, 58b positioned at predetermined angles, as previously described. Optionally, the barrels 58a, 58b can be removably mated to the connector 72 to allow the lengths of the barrels 58a, 58b to be selected by the surgeon.

The connector 72 can have a variety of configurations, shapes and sizes. As shown in FIG. 11, the connector 72 extends between the barrels 58a, 58b and a proximal end 72a, a distal end 72b, and a T-shaped slot 74 extending therebetween. The slot 74 is adapted to mate to the corresponding T-shaped member 68 formed on the elongate member 52. The slot 74 can optionally include a retaining element for temporarily securing the guide member 56 to the elongate member 52. While a variety of retaining elements can be used, in one embodiment the retaining element can be a ball plunger (not shown) disposed within the T-shaped slot 74 and adapted to sit in a corresponding detent (not shown) formed on the elongate member 52. The ball plunger depresses upon insertion of the guide member 56 onto the elongate member 52, and once the guide member 56 abuts the stop member 70, the ball plunger is aligned with the detent and thus extends into the detent in the elongate member 52 to temporarily secure the guide member 56 to the elongate member 52.

In use, the shaft 54 is inserted through the elongate member 52 and the distal end 54b of the shaft 54 is engaged to the fixation plate 60, as shown in FIG. 8. Preferably, the alignment mechanism 53 formed on the distal end 52b of the elongate member 52 is aligned with the plate 60 while the shaft 54 is being manipulated to engage the plate 60. A guide member 56 having barrels 58a, 58b positioned at the appropriate angle and having the appropriate lengths is selected, and is slid onto the elongate member 52 in a proximal-to-distal direction. Once the guide member 56 is fully attached to the elongate member 52, one or more tools can be inserted through the barrels 58a, 58b to secure the plate 60 to a patient's spine.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A modular drill guide, comprising:
    an elongate member having a proximal end and a distal end;
    a shaft coupled to the elongate member and having a proximal end and a distal mating end adapted to mate to a spinal fixation plate; and
    at least one guide member removably mated to the elongate member and having first and second barrels formed therein and defining a bore or receiving a tool, the guide member further including a connector having a mating element formed thereon for mating to the elongate member, the mating element being disposed on the proximal end of the connector and being adapted to mate to a corresponding mating element formed on the distal end of the elongate member.

2. The modular drill guide of claim 1, wherein the elongate member has an inner lumen extending therethrough between the proximal and distal ends thereof, and wherein the shaft is rotatably disposed within the inner lumen of the elongate member.

3. The modular drill guide of claim 2, wherein the elongate member includes a locking element effective to prevent rotation of the shaft with respect to the elongate member.

4. The modular drill guide of claim 1, wherein the mating element has a connection selected from the group consisting of an interference fit, dovetail connection, a snap-fit connection, and a tongue-and-groove connection.

5. The modular drill guide of claim 1, wherein the guide member is slidably matable onto the elongate member in a proximal-to-distal direction.

6. The modular drill guide of claim 1, wherein the distal mating end of the shaft includes an engagement mechanism formed thereon for mating with a spinal fixation plate.

7. The modular drill guide of claim 6, wherein the engagement mechanism is selected from the group consisting of threads, a hook member, a twist-lock member, and a snap-fit member.

8. The modular drill guide of claim 6, wherein the proximal end of the shaft includes a gripping element formed thereon.

9. The modular drill guide of claim 1, wherein the distal end of at east one of the elongate member and the guide member includes an alignment mechanism adapted to align the modular drill guide with a spinal fixation plate engaged by the distal mating end of the shaft.

10. The modular drill guide of claim 9, wherein the alignment mechanism is selected from the group consisting of at least one protrusion adapted to fit within a corresponding detent formed on a spinal fixation plate, and at least one flange adapted to be positioned adjacent an edge of a spinal fixation plate.

11. The modular drill guide of claim 1, wherein the mating element has a snap-fit connection.

12. The modular drill guide of claim 1, wherein the connector further includes a bore extending therethrough for receiving a portion of the shaft.

13. The modular drill guide of claim 1, wherein the guide member mates to one of a distal portion and a middle portion of the elongate member.

14. The modular drill guide of claim 1, further comprising a handle member mated to at least one of the elongate member and the guide member.

15. The modular drill guide of claim 14, wherein the handle member is rotatably mated to at least one of the elongate member and the guide member.

16. The modular drill guide of claim 1, wherein at least one barrel is adapted to receive a tool selected from the group consisting of an awl, a drill bit, a fastening element, and a driver device.

17. A modular drill guide, comprising:
    a shaft having a proximal end and a distal end adapted to engage a spinal fixation plate;
    at least one guide member removably and replaceably matable to the shaft, the guide member having a connector member with at least one bore extending therethrough for receiving at least a portion of the shaft, and at least one barrel formed thereon and defining a lumen for receiving a tool; and
    a mating body for removably and replaceably mating the guide member to the shaft, the mating body having an inner lumen formed therein for receiving at least a portion of the shaft, and a proximal end and a distal end, and wherein the connector member has a generally elongate cylindrical shape having a proximal end and a distal end, the proximal end of the connector being adapted to removably mate to the distal end of the mating body.

18. The modular drill guide of claim 17, wherein the shaft extends through the bore in the connector member and through the inner lumen in the mating body when the guide member is mated to the mating body.

19. The modular drill guide of claim 17, wherein the at least one barrel on the guide member is formed on the distal end of the connector member.

20. The modular drill guide of claim 17, further comprising a handle member extending outward from the mating body to facilitate grasping of the device.

21. The modular drill guide of claim 17, wherein the distal end of the connector includes an alignment mechanism adapted to align the guide member with a spinal fixation plate engaged by the distal end of the shalt.

22. A modular drill guide kit, comprising:
- an elongate member having a proximal, handle end and a distal mating end adapted to removably mate to a spinal fixation plate; and
- a plurality of guide members removably and replaceably matable to the elongate member, each guide member having first and second barrels formed thereon and disposed at a predetermined angle with respect to a longitudinal axis of the elongate member, and a connector having a first end mated to the first barrel and a second, opposed end mated to the second barrel, the connector further including a mating element formed between the first and second ends thereof for mating the guide member to the elongate member, the mating element disposed on a proximal end of the connector and adapted to mate to a corresponding mating element formed on the distal end of the elongate member, each of the plurality of guide members having at least on barrel with a predetermined angle different from the predetermined angle of the at least one barrel formed on another one of the plurality of guide members.

23. The modular drill guide kit of claim 22, wherein the distal mating end of the elongate member includes an engagement mechanism formed thereon for mating with a spinal fixation plate.

24. The modular drill guide kit of claim 22, wherein the distal end of the elongate member includes an alignment mechanism adapted to align the modular drill guide with a spinal fixation plate engaged by the distal mating end of the shaft.

25. The modular drill guide kit of claim 22, wherein the mating element has a snap-fit connection.

26. The modular drill guide kit of claim 22, wherein the connector further includes a bore extending therethrough for receiving a portion of the shaft.

27. The modular drill guide kit of claim 22, wherein the guide member mates to one of a middle portion and a distal portion of the elongate member.

28. The modular drill guide kit of claim 22, wherein each barrel has a predetermined angle in the range of about 0° to 15°.

* * * * *